(12) United States Patent
Lai

(10) Patent No.: US 6,169,779 B1
(45) Date of Patent: Jan. 2, 2001

(54) DATA ACQUISITION SEQUENCE FOR COMPUTED TOMOGRAPHY SCANNERS

(75) Inventor: Ching-Ming Lai, Wakefield, MA (US)

(73) Assignee: Analogic Corporation, Peabody, MA (US)

(*) Notice: Under 35 U.S.C. 154(b), the term of this patent shall be extended for 0 days.

(21) Appl. No.: 09/175,655

(22) Filed: Oct. 20, 1998

(51) Int. Cl.[7] ............................................. A61B 6/03
(52) U.S. Cl. .............................. 378/19; 378/15; 378/901
(58) Field of Search ............................. 378/4, 15, 19, 378/901

(56) References Cited

U.S. PATENT DOCUMENTS 5,126,938 * 6/1992 Oda ......................................... 378/13
5,257,183 * 10/1993 Tam ......................................... 378/4

* cited by examiner

*Primary Examiner*—David V. Bruce
(74) *Attorney, Agent, or Firm*—McDermott, Will & Emery

(57) ABSTRACT

In an improved computed tomography data acquisition sequence, fan-beam or cone-beam projection data are collected in a manner which avoids the need for interpolation during reordering to parallel-beam projections. Rather than sampling all channels in a detector array as a whole at each rotation angle, the channels are sampled sequentially in a predetermined number of groups. A first group is sampled, and following a delay, subsequent groups are sampled. The delay is determined by the angular spacing of the detectors and the gantry rotation speed. The projections within a group can be sampled either simultaneously or successively. The invention is applicable to medical and material imaging systems.

49 Claims, 5 Drawing Sheets

DATA ACQUISITION SEQUENCE FOR COMPUTED TOMOGRAPHY SCANNERS

BACKGROUND OF THE INVENTION

In a conventional third-generation computed tomography (CT) scanner, a plurality of detectors, more generally detector channels, 53 are positioned in a row 52 along a circular arc centered about an X-ray source 54 as shown in FIG. 1. The detector array 52 and the X-ray source 54 together are mounted on a rotatable device called a gantry. During a scan, the gantry rotates about an object 55 to be imaged. Data are acquired as fan-beam projections 50 of the object 55 at successive increments of gantry rotation angle. The fan beam projections at successive rotation angles can be reconstructed to form an image of a slice through the object through which the X-rays have passed. Alternatively, the fan-beam projections are reordered into sets of parallel-beam projections, each at a corresponding common projection angle, prior to reconstruction of the image. Parallel-beam reconstruction is generally preferred to fan-beam reconstruction because it requires fewer computations and therefore provides faster results.

Each set of parallel-beam projections thus represents a collection of projection data at a corresponding projection angle $\phi$ for all detectors. Suppose the angular spacing of the detectors is $\delta$ (i.e., the angle subtended by the portion of the fan beam projected onto one detector segment of the detector array) and the rotation angle of the gantry is $\theta$. As can be seen from FIG. 2, the projection angle $\phi$ of the jth channel of the detector array is related to gantry rotation angle $\theta$ and detector angular spacing $\delta$ by:

$$\phi = \theta - (j - j_o) * \delta, \quad (1)$$

where $j_o$ is the central detector channel, which lies on the X-ray path projecting from the source 54 through the center of rotation 20.

Fan-beam projection data are sampled at successive rotation angles of interval $\Delta\theta$. In the specific case where the rotation-angle interval $\Delta\theta$ is equal to the detector angular spacing, i.e., $\Delta\theta = \delta$, the process of reordering from fan-beam projections to parallel-beam projections is relatively straightforward. A map of projection angle $\phi$ versus detector channel number j for this case is plotted in FIG. 3. Each vertical column 22 of data points on the map represents the projection angles of the collected projection data $P_j(\theta)$ at detector channel j at successive rotation angles $\theta$. Each diagonal row 24 of data points represents the projection angles of fan beam data collected by the detector array at a single rotation angle $\theta_k$. Each horizontal row 26 of data points on the map constitutes the reordered parallel-beam data $R_j(\phi)$ used for image reconstruction at projection angle $\phi$. Therefore, in the simple case where $\Delta\theta = \delta$, the reordering from fan-beam projection data to parallel-beam projection data is simply a data sorting procedure.

CT scanners are often configured such that projection data is collected at a rotation-angle interval greater than the detector angular spacing, i.e., $\Delta\theta > \delta$, for reducing the data collection rate or for hastening the reconstruction process. Such a configuration affects the fan-beam to parallel-beam reordering procedure. If $\Delta\theta = 3\delta$, for example, the parallel-beam projection data cannot simply be sorted out from the fan-beam projection data, as only one out of three parallel-beam projections coincides with a fan-beam projection. The remaining two-thirds of the parallel-beam projection data must be interpolated from fan-beam projections at successive rotation angles. This holds true for conventional third-generation scanners having a single detector row (FIG. 1), and for cone-beam scanners having multiple detector rows (FIG. 4). Interpolation has a filtering effect on the data, which degrades spatial resolution of the reconstructed image. It is therefore desirable to avoid such interpolation during reordering.

SUMMARY OF THE INVENTION

The present invention is directed to a method of and system for data acquisition which avoids the need for interpolation of data from adjacent rotation angles during reordering of data. The present invention takes advantage of the rotation of the gantry and the fact that during the transition between rotation angles at increments $\Delta\theta$, detectors are moving through positions which correspond accurately to a projection angle $\phi$. If the appropriate detectors are sampled at the proper rotation angles between the rotation angles of increments $\Delta\theta$, referred to herein as sub-rotation angles, then the resulting data is properly aligned for reordering, without the need for the interpolation.

In accordance with one embodiment of the method of the present invention, data is collected from a plurality of detector channels of a detector array during a CT scan of the type where at least a source of a diverging beam of radiation projected toward the detector array is rotatable about a rotation axis through a plurality of rotation angles $\theta$, and the angle $\delta$ subtended by the part of the beam projected toward each of the detector channels is smaller than the incremental angle $\Delta\theta$ between successive rotation angles. The method comprises collecting data from the detector channels in a predetermined sequence so that all of the data represents parallel projection data at the projection angles without the need to interpolate any of the parallel projection data.

In accordance with another embodiment of the system of the present invention, a CT scanning system comprises:

a detector array including at least one row of detector channels;

a source of energy defining a diverging beam of radiation directed toward the array, wherein at least the source is rotatable about a rotation axis through a plurality of rotation angles $\theta$ and the angle $\delta$ subtended by the part of the beam projected toward each of the detector channels is smaller than the incremental angle $\Delta\theta$ between rotation angles; and a subsystem for acquiring data from the detector array within a predetermined time interval as the rotation of the source passes through each of the rotation angles;

wherein data is collected from the detector channels in a predetermined sequence so that all of the data represents parallel projection data at the projection angles without the need to interpolate any of the parallel projection data.

Thus, rather than the conventional practice of sampling all channels in the array at each rotation angle, in the technique of the present invention, data are sampled in a preselected number of groups of detector channels. In this manner, parallel-beam projection data can be obtained from the fan-beam projection data without interpolation. This technique is applicable to both conventional fan-beam scanners and cone-beam scanners, and is applicable to both simultaneously sampled systems and successively sampled systems.

In one embodiment, the present invention comprises a method of acquiring projection data in a computed tomography system. The system includes an energy source and a detector array having a plurality of channels rotatable about an object to be imaged for interrogating the object at incremental rotation angles. At each incremental rotation angle, first fan-beam projection data is sampled from a first group of the detector elements. Each fan-beam projection is oriented at a projection angle different from other projections in the first group. During transition of the detector array and source to a subsequent incremental rotation angle, second fan-beam projection data are sampled from a second group of detector channels paired and interleaved with the first group of detector channels. Sampling of data at the second group preferably occurs when the detector channels of the second group are in such a rotational position that the projection angle of the first group of detector channels is substantially aligned with the projection angle of the second group of detector channels for each detector channel pair.

The channels in the detector array have an angular spacing $\delta$ which is smaller than the rotation angle interval $\Delta\theta$.

In a preferred embodiment where $\Delta\theta=2\delta$, at each incremental rotation angle, fan-beam projection data are sampled from, for example, odd-numbered detector channels as a group. Each fan-beam projection has a different projection angle with respect to those projections collected from other detector channels in the group. During transition of the detector array and source to a subsequent incremental rotation angle, another set of fan-beam projection data are sampled from, for example, even-number detector channels as a group. The fan-beam projection data collected at even-number detector channels are paired and interleaved with data from odd-number detector channels. Sampling takes place preferably when the even-number detector channels are in such position that the projection angles of the even-number detector channels are substantially aligned with that of the odd-number detector channels for each detector channel pair.

In another preferred embodiment, the rotation angular interval $\Delta\theta$ is substantially an integer multiple q of the detector channel angular spacing $\delta$, and the fan-beam projection data are sampled in q groups.

The detector channels in a group may be sampled simultaneously or successively at each discrete rotation angle. The detector array may comprise a single row of detector elements for fan-beam scanning or multiple rows of detector elements for cone-beam scanning in either stationary (non-helical) or translational (helical) scan mode. The detector angular spacing $\delta$, the sampling interval $\Delta\theta$, the gantry rotation speed $\omega$, and the successive sampling rate $1/\tau$ preferably satisfy the relationship:

$$\Delta\theta = q*\delta'_{eff} = q\delta - \omega\tau, \quad (2)$$

where q is an integer and where the detector array is divided into q groups. Each group is preferably sampled at a rotational angle offset of $\delta'_{eff}$ following the previous group where $\delta'_{eff}=\delta-\omega\tau/q$. Simultaneous sampling can be treated as a special case of successive sampling where $\tau=0$ and $\delta'_{eff}=\delta$.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

The principles of the present invention are best understood by first studying the limitations of the conventional process in further detail. An illustrative example is now given, with reference to FIG. 5.

Figure 4:
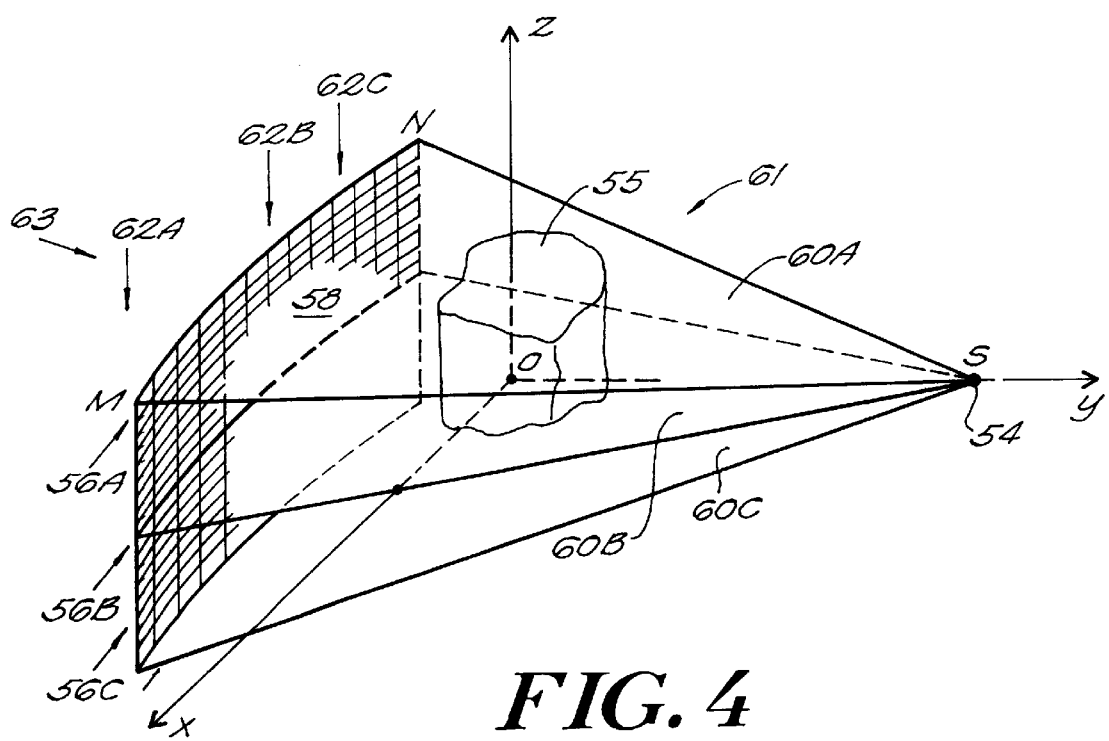
FIG. 4 is a perspective view of a cone-beam CT scanner employing a two-dimensional detector array having M rows and N columns of detector channels.
Figure 5:
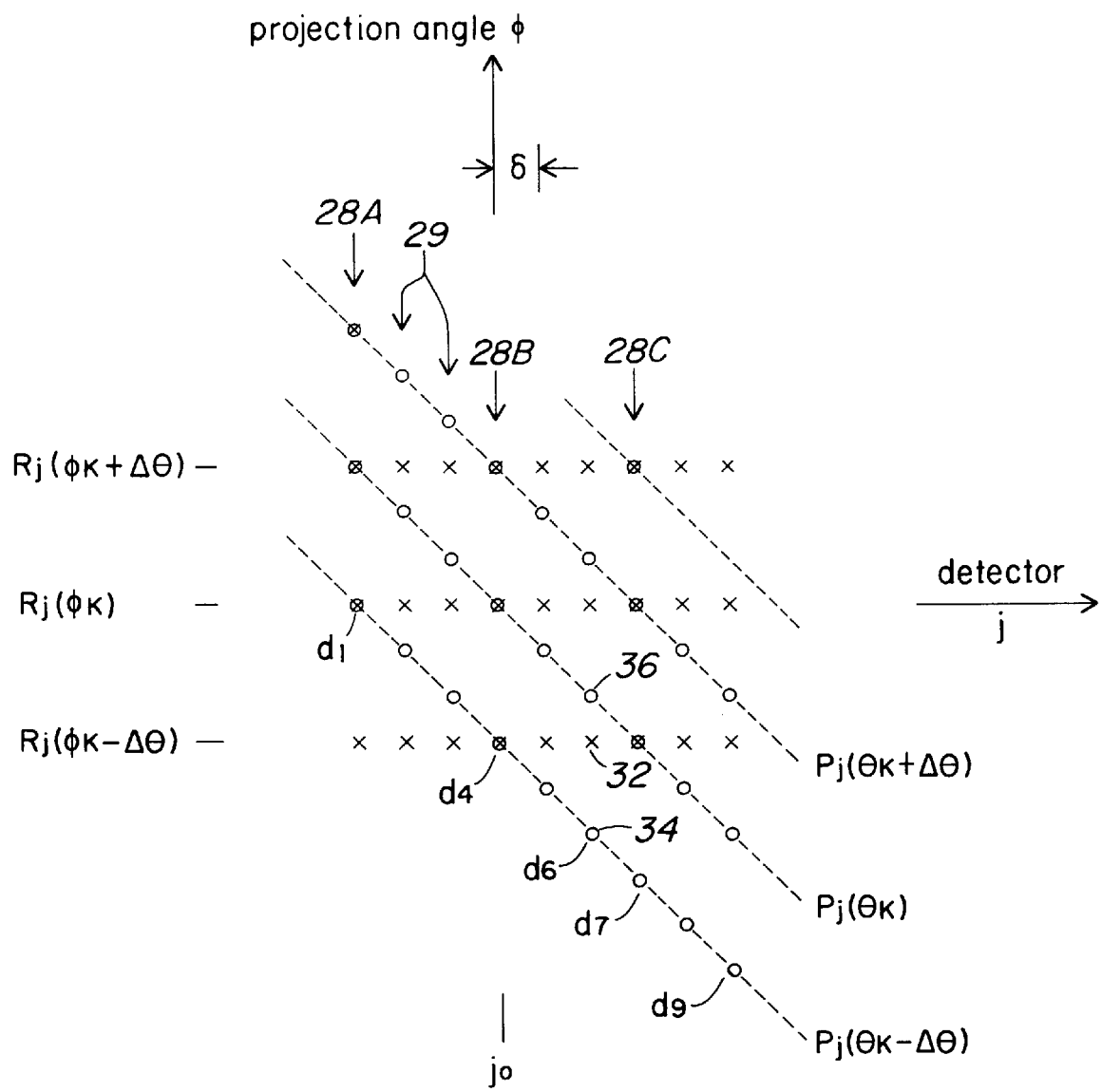
FIG. 5 is a map of data points of collected fan-beam projection data $P_j(\theta)$ and reordered parallel-beam projection data $R_j(\phi)$ illustrating the need for interpolation when the system rotation angle interval is greater than the detector angular spacing, i.e. $\Delta\theta>\delta$.

FIG. 5 is a map of a partial number of data points for collected fan-beam projection data $P_j(\theta)$ and reordered parallel-beam data $R_j(\phi)$ according to a conventional data collection technique in a system where the rotation angle interval is greater than the detector angle spacing, for example a three-to-one ratio: $\Delta\theta=3\delta$. The projection angle $\phi$ of the acquired data is plotted as a function of detector channel number j. For clarity, only the data points of projections from nine detector channels ($d_1 \ldots d_9$) over three fan-beam rotation angles ($\theta_k-\Delta\theta$, $\theta_k$, $\theta_k+\Delta\theta$) are shown, plotted in circles along a dashed line for each rotation angle. It will be appreciated, however, that for a typical CT scanner many more data points, projections and detector channels are utilized. $P_j(\theta_k)$ represents the collected fan-beam projection of the jth detector channel at a rotation angle of $\theta'_k$. Likewise, $R_j(\phi_k)$ represents the jth channel reordered projection at a parallel-beam projection angle of $\phi_k$, interpolated from the fan-beam projections. The locations of one set of the parallel-beam projections $R_j(\phi_k)$ are plotted in crosses. Note that, for ideal reconstruction, within the field of view the data points of the collection of parallel-beam projections within a set should be parallel to each other, and as shown in the map of FIG. 4 lie substantially on a horizontal line, i.e., they should share substantially the same projection angle $\phi$.

Assuming a detector array of N detector channels, and assuming $j_o$ is the central channel, for a given detector channel j, based on Equation (1), the parallel-beam projection angle $\phi_k$ is related to the rotation angle $\theta_k$ by:

$$\phi_k = \theta_k - (j-j_o)*\delta = \theta_k - (j-j_o)*\Delta\theta/3, \quad (3)$$

where k is an integer with $\theta_k = k*\Delta\theta$, and $j=1,2,\ldots,N$.

Let m be the truncated integer and r the remainder of the quotient $-(j-j_o)/3$, that is:

$$-(j-j_o)/3 = m+r. \quad (4)$$

If linear interpolation is used to interpolate the parallel-beam data $R_j(\phi_k)$ from the collected fan-beam data $P_j(\theta_k)$, then:

$$R_j(\phi_k) = (1-r)*P_j(\theta_k + m*\Delta\theta) + r*P_j(\theta_k + (m+1)*\Delta\theta), \quad (5)$$

or, $$R_j(\phi_k) = (1-r)*P_j(\theta_{k+m}) + r*P_j(\theta_{k+m+1}). \quad (6)$$

For the general case of $\Delta\theta = q*\delta$ with $q>1$, the above relationships are applicable except that the constant 3 in Equations (3) and (4) is replaced by the more generalized constant q.

If q is an integer, the remainder r will be zero in every channel which is a multiple of q. In the latter case, as seen in FIG. 5, the position of the reordered projection $R_j(\phi_k)$ will align with the position of the collected projection $P_j(\theta_{k+m})$ in detector channels which are multiples of q (in the example every third channel) and indicated as the detector channels, indicated by data points $d_1$, $d_4$, $d_7$, and numerals 28A, 28B, 28C in FIG. 5. However, the remaining channels indicated by data points $d_2$, $d_3$, $d_5$, $d_6$ (indicated, for example, at 29 in FIG. 5), generalized as $N*(q-1)/q$ in total number, will require the interpolation given in Equation (6) to generate data values for the parallel-projection data, for example, the data point 32. Referring still to FIG. 5, the interpolation given by Equation (6) will derive, for example, a data value for data point 32 from the collected fan-beam data values for detector channel at data points $d_6$ at rotation angles $\theta_k - \Delta\theta$ (reference numeral 34) and $\theta_k$ (reference numeral 36). As described above, the interpolation degrades the spatial resolution of the reconstructed image.

Figure 6:
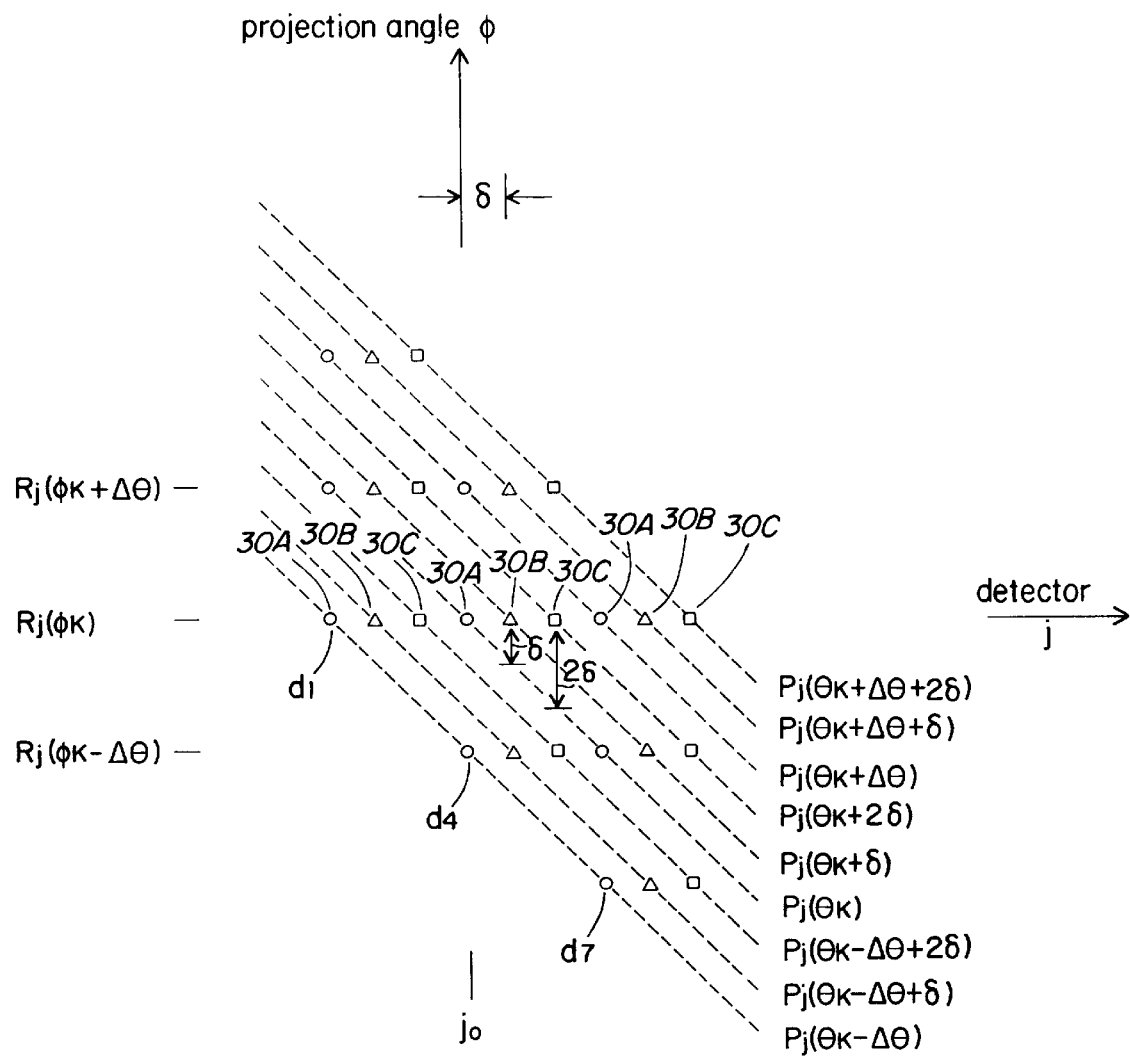
FIG. 6 is a map of data points of collected projection data $P_j(\theta)$ and reordered parallel-beam projection data $R_j(\phi)$ collected in accordance with a preferred embodiment of the data acquisition sequence of the present invention; the data are collected in three groups, the first group is plotted data points shown as circles, the second group is plotted data points shown as triangles, and the third group is plotted data points shown as squares, along diagonal lines.

The present invention is directed to a data sampling technique which avoids the need for such interpolation. Instead of sampling fan-beam projection data at all detectors at each rotation angle $\theta$, the detectors are instead divided into q groups. The groups of detectors are sampled sequentially with the sequence preferably repeating through an entire scan. For example, in the case where q=3, each detector group consists of detectors spaced at intervals of every three channels as shown in FIG. 6. The first group, having data points plotted in circles along a dashed line, is sampled at rotation angle $\theta_k$. The second group, having data points plotted in triangles on another dashed line, is sampled at rotation angle $\theta_k + \delta$, an additional rotation angle of $\delta$ following the first group. Likewise, the third group, having data points plotted in squares on a dashed line, is sampled at rotation angle $\theta_k + 2\delta$, at an additional rotation angle of $\delta$ following the second group. As mentioned, the sequence preferably, although not necessarily, is repeated throughout the scan. The detectors of the first, second and third groups are also spatially sequenced the row(s) in the detector array, so that viewing the detectors of a row from one side of the detector array to the other side, a detector of the first group is followed by a detector of the second group, which in turn is followed by a detector of the third group, with the sequence repeating preferably for the entire row of the array.

The present invention accomplishes this by first sampling the group 1 data, such as the data at each data point 30A indicated in the map shown in FIG. 6, at a time when the gantry reaches each of the fan beam rotation angles of $(\theta_k - \Delta\theta)$ (during the fan beam projection $P_j(\theta_k - \Delta\theta)$; $\theta_K$ (during the fan beam projection $P_j(\theta_K)$ which is three projection intervals later); $(\theta_k + \Delta\theta)$ (during the fan beam projection $P_j(\theta_k + \Delta\theta)$ which is still another three projection intervals later), etc. As the gantry continues to rotate through each of these data points, sampling of the group 2 data, such as the data at each of the data points 30B, is delayed by an additional sub-rotation angle of $\delta$, until a time when the gantry reaches each rotation angle of $(\theta_k - \Delta\theta + \delta)$; $(\theta_K + \delta)$; $(\theta_k + \Delta\theta + \delta)$; etc. Likewise, the sampling of group 3 data, such as the data of each data points 30C, is delayed until the gantry reaches a rotation angles of $(\theta_k - \Delta\theta + 2\delta)$; $(\theta_K + 2\delta)$; $(\theta_k + \Delta\theta + 2\delta)$; etc. In this manner, where $\delta$ is substantially equal to the angular spacing of the detector elements (i.e., the angle of the portion of the diverging beam which is projected onto one detector including one half the spacing (if any) between the adjacent detectors which is preferably a constant across the entire row(s) of the detector array), the positions of all fan-beam data collected (such as 30A, 30B, 30C marked by data points indicated as circles, triangles, and squares respectively) are sequentially acquired and correspond with the positions of reordered parallel-beam data (such as $R_j(\phi_k)$ marked by crosses in FIG. 5) and interpolation is not necessary for reordering.

The principles of the data collection technique of the present invention are now described in further detail. For example, let j' be the integers $1, 4, \ldots, j_o-3, j_o, j_o+3, \ldots N-2$, such that $j'-j_o$ is divisible by 3, in other words, $$-(j'-j_o)/3 = m, \quad (7)$$

where m is an integer. Applying Equation (3) to the first group, with $j=j'$:

$$\phi_{k1} = \theta_k - (j'-j_o)*\delta. \quad (8)$$

For the second group, $j=j'+1$, since each channel number is one greater than the first group, the rotation angle $\theta_k$ of Equation (3) is replaced by $\theta_k + \delta$, because the data are sampled at a later time, with the rotation angle advanced an additional angle of $\delta$. Therefore, the parallel-beam projection angle of the second group becomes:

$$\phi_{k2} = (\theta_k + \delta) - (j'+1-j_o)*\delta = \theta_k - (j'-j_o)*\delta. \quad (9)$$

Similarly, for the third group:

$$\phi_{k3} = (\theta_k + 2\delta) + (j'+2-j_o)*\delta = \theta_k - (j'-j_o)*\delta. \quad (10)$$

Equations (8), (9), and (10) demonstrate that all three groups have the same parallel-beam angle $\phi_k$. That is, $$\phi_{k1} = \phi_{k2} = \phi_{k3} = \theta_k - (j'-j_o)*\delta = \theta_k - (j'-j_o)*\Delta\theta/3 = \theta_k + m*\Delta\theta. \quad (11)$$

Therefore, with this sampling sequence, parallel-beam projections $R_j(\phi_k)$ can be obtained by sorting out the fan-beam projections $P_j(\theta_k)$ collected in three groups as:

$$R_j(\phi_k) = P_j(\theta_k + m*\Delta\theta) = P_j(\theta_{k+m}) \quad (12)$$

where $j=1, 4, \ldots, j_o-3, j_o, j_o+3, \ldots, N-2$, for the first group, $j=2, 5, \ldots, j_o-2, j_o+1, j_o+4, \ldots, N-1$, for the second group, and $j=3, 6, \ldots, j_o-1, j_o+2, j_o+5, \ldots, N$, for the third group.

Figure 1:
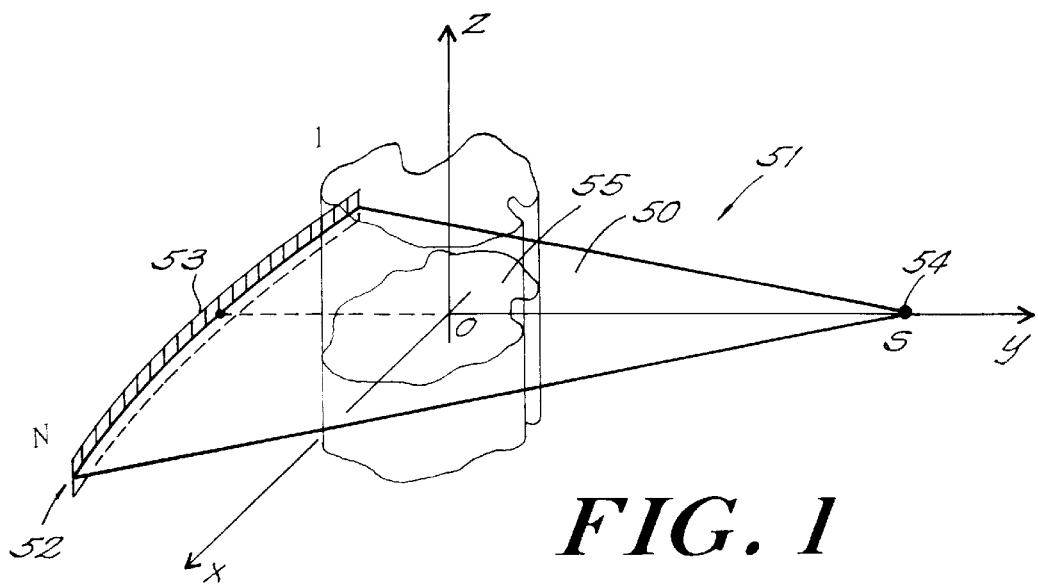
FIG. 1 is a perspective view of a third-generation CT scanner, wherein a single row of detector channels and an X-ray source are mounted on a gantry which rotates about the z-axis during a scan.

In the scanner shown in FIG. 1, a single row array of detector channels is shown and the data can be sequentially acquired with each data point of the map shown in FIG. 6 representing data acquired by a single detector channel. In the cone-beam scanner shown in FIG. 4, multiple rows of detectors are used. Assume that the detector array 63 consists of M rows 56 of detectors with N channels 62 per row.

At a given rotation angle θ, the data collected by each row 56 of detectors resemble the fan-beam projections collected by a conventional single-row detector scanner. From multiple rows of detectors 56A, 56B, 56C, multiple fan-beam projections 60A, 60B, 60C are collected. They are divergent from the X-ray source 54 in both row and column directions and thus are referred to as cone-beam projections. It should be appreciated that the principles of the present invention be applied to the cone-beam scanner as well.

Like the conventional scanner, there are certain advantages to reordering the collected cone-beam projections to parallel-beam projections for reconstructing images. In the cone-beam scanner, these parallel-beam projections are commonly reordered from a single row of cone-beam data, independent of other rows. In other words, the reordered cone-beam data can be envisioned as multiple sets of parallel-beam projections, with each set generated from the fan-beam data collected by a single row of detectors.

Assume that $P_{ij}(\theta_k)$ represents the fan-beam projection acquired by a detector at the ith row and the jth column, or jth channel, of the two-dimensional detector array at a rotation angle of $\theta_k$. Similarly, $R_{ij}(\phi_k)$ represents the parallel-beam projection to be generated at a projection angle of $\phi_k$.

If the rotation-angle interval Δθ of the system is greater than the detector angular spacing δ, namely, $\Delta\theta = q*\delta$ with q>1, and assuming linear interpolation is used, then similar to Equation (6), the parallel beam projections $R_{ij}(\phi_k)$ in the cone-beam system are represented by:

$$R_{ij}(\phi_k) = (1-r)*P_{ij}(\theta_{k+m}) + r*P_{ij}(\theta_{k+m+1}), \quad (13)$$

where m and r are defined in Equation (4) with $j_o$ as the central column of the 2D detector array.

For the purpose of example, assume again that q=3. As described above, if all detector channels in the array are sampled at each rotation angle θ, then interpolation is needed to generate a majority of the parallel-beam projections. In order to avoid the interpolation process, the sampling sequence of the present invention partitions the two-dimensional detector array into individual groups; three groups in the present example. Each group consists of the detectors in the M rows of detectors preferably at a three-column interval. With respect to the first group, the detectors of the second group are preferably offset by one column and the detectors of the third group are preferably offset by two columns. The second and third groups are sampled at the time when the rotation angle θ reaches an additional sub-rotation angle of δ and 2δ, respectively, following the first group. If the first group is sampled at rotation angle of $\theta_k$, the second group is sampled at rotation angle of $\theta_k+\delta$ and the third group is sampled at $\theta_k+2\delta$. The sequence is preferably, but not necessarily, repeated throughout the scan.

Assuming this grouping, and employing the derivation of Equations (8) through (11), the reordered parallel-beam projections $R_{ij}(\phi)$ can be obtained from the collected cone-beam projections $P_{ij}(\theta)$ as:

$$R_{ij}(\phi_k) = P_{ij}(\theta_k + m*\Delta\theta) = P_{ij}(\theta_{k+m}), \quad (14)$$

without the need for interpolation, where the row number i=1, 2, . . . , M, and the column number j=1, 4, . . . , $j_o$−3, $j_o$, $j_o$+3, . . . , N−2 for the first group, j=2, 5, . . . , $j_o$−2, $j_o$+1, $j_o$+4, . . . , N−1 for the second group, and j=3, 6, . . . , $j_o$−1, $j_o$+2, $j_o$+5, . . . , N for the third group.

The above discussion assumes that the system operates in a simultaneous sampling configuration. In a simultaneously-sampled system, all detector elements in the array (or in a group in the case of the present invention) are sampled at the same time, at each rotation angle θ.

It should be appreciated that sampling in a CT system of the relevant detectors during each projection is not always simultaneous; it is quite common for a system to employ successive sampling where each element in the array is activated or sampled, individually (or in groups) and successively during a scan. This introduces a latency between the timing of the sampling of successive channels. Because the gantry is rotating, this latency introduces a slip in the projection angle $\phi_k$ of each channel; the slip being directly related to latency of that channel. The following discussion is a derivation of system equations taking this latency into account.

Assume the latency per channel to be τ, which is equivalent to a sampling rate of 1/τ. Also, assume ω to be the angular velocity of the gantry, and assume that the data are individually sampled in sequential order from channel 1 to channel N with clockwise gantry rotation. According to the geometry of FIG. 2, by the time channel j is sampled, the projection angle of channel j will gain an additional angle of $(j-j_o)*\omega\tau$ with respect to the central channel $j_o$. The parallel-beam projection angle in the successive sampling sequence therefore becomes:

$$\phi_k = \theta_k - (j-j_o)*\delta + (j-j_o)*\omega\tau. \quad (15)$$

Equation (15) can be rewritten as:

$$\phi_k = \theta_k - (j-j_o)*\delta_{eff}, \quad (16)$$

with:

$$\delta_{eff} = \delta - \omega\tau. \quad (17)$$

Equations (16) and (17) indicate that in the case of successive sampling, the parallel-beam projection angle $\phi_k$ is equivalent to simultaneous sampling case of Equation (3), except that the detector spacing δ of Equation (3) is replaced by an effective detector angular spacing of $\delta_{eff}$, decreased (compressed) from the actual spacing δ by an amount ωτ as a result of sampling latency.

Figure 2:
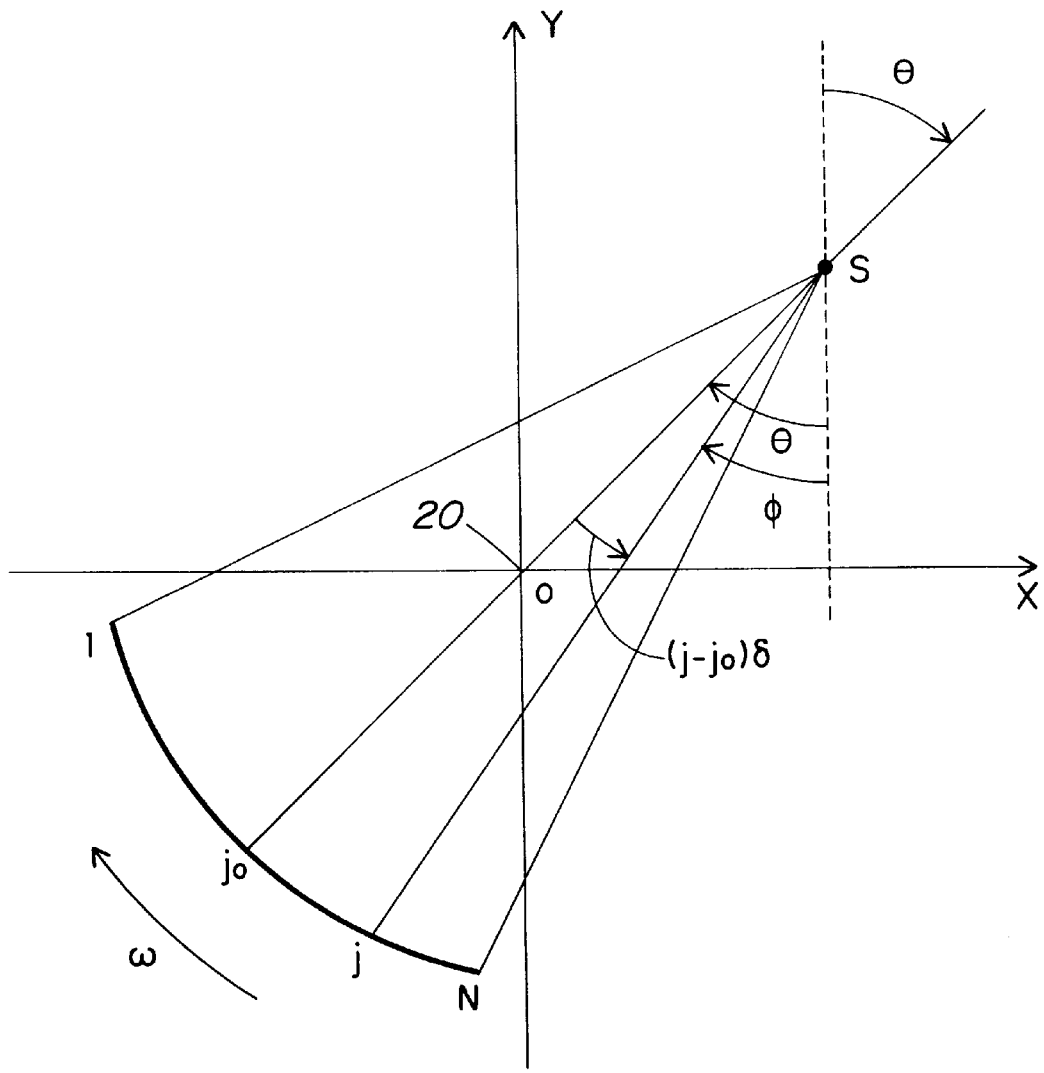
FIG. 2 is a top view of the scanner of FIG. 1 illustrating the relationship between the projection angle $\phi$ of the projection data, the rotation angle $\theta$ of the gantry, the angular spacing $\delta$ between adjacent detectors, and the detector number j.
Figure 3:
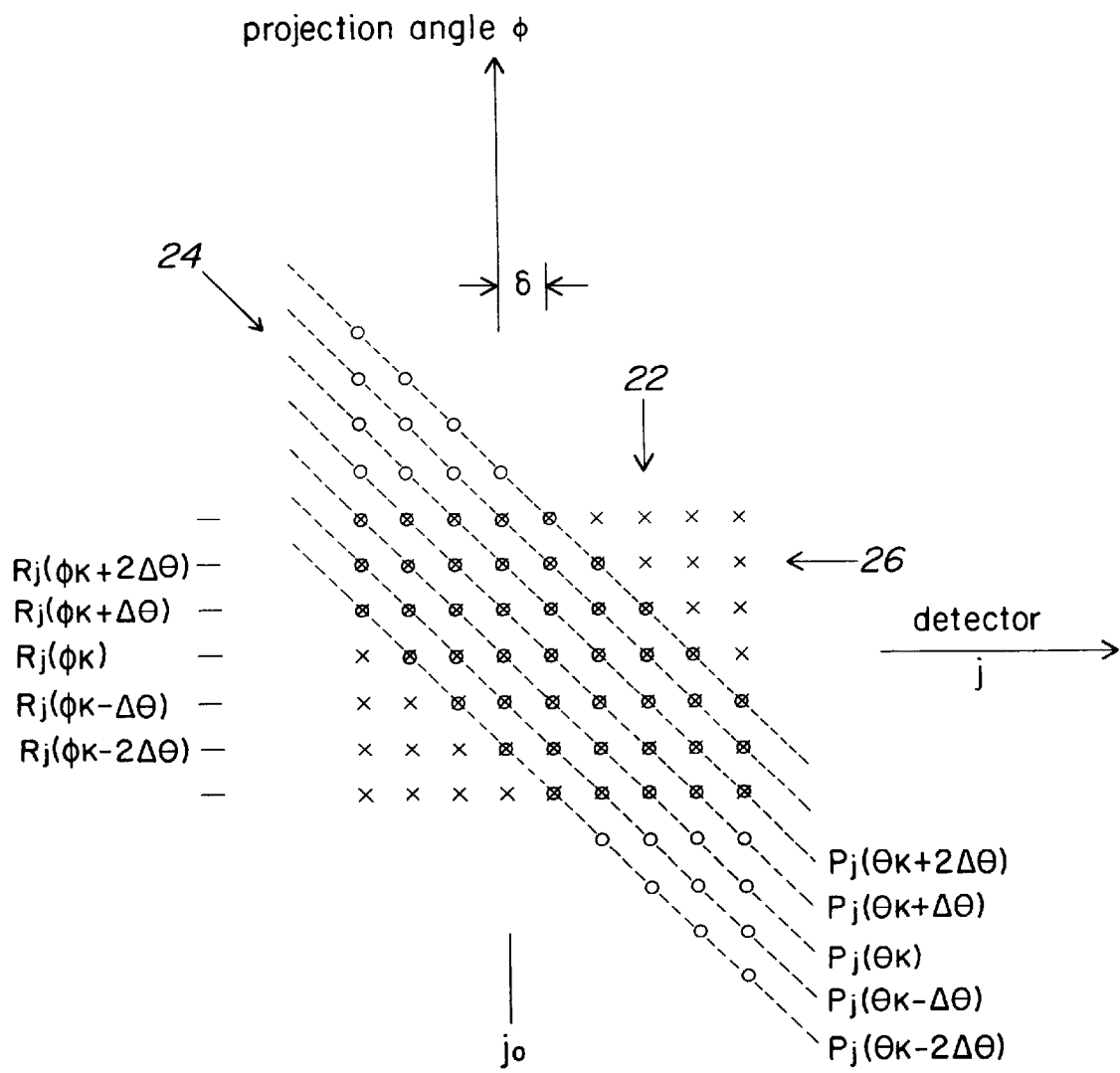
FIG. 3 is a map of data points representing collected fan-beam projection data $P_j(\theta)$, plotted in circles along a diagonal line as a function of detector number j, and reordered parallel-beam projection data $R_j(\phi)$ used for reconstruction, marked in crosses along a horizontal line, for a system wherein the rotation angle interval is equal to the detector angular spacing, i.e. $\Delta\theta=\delta$.

If gantry rotation in FIG. 2 is counterclockwise, the sign of the gantry angular velocity ω is reversed. In this case, $\delta_{eff}$ will be equivalent to the angular spacing increased (stretched or extended) by an amount ωτ. Therefore, by substituting $\delta_{eff}$ for δ, Equations (3) through (6), applicable to simultaneous sampling, can be applied to successive sampling.

To illustrate the application of successive sampling to the present invention, assume that q=3, and that the projection angle of each channel includes a slip angle of ωτ per sampling channel. Since each group is sampled successively at every three channels of the detector array, the slip angle at channel j' in the group is represented by $\omega\tau*(j'-j_o)/3$ relative to the central channel $j_o$.

Referring to Equation (8), the projection angle for the first group becomes:

$$\phi_{k1} = \theta_k - (j'-j_o)*\delta + \omega\tau*(j'-j_o)/3 \quad (18)$$

or, $$\phi_{k1} = \theta_k - (j'-j_o)*\delta'_{eff}, \quad (19)$$

where:

$$\delta'_{eff} = \delta - \omega\tau/q. \quad (20)$$

The equations derived above for simultaneous sampling are therefore applicable to successive sampling by substituting $\delta'_{eff}$ for $\delta$ in Equations (8) through (14). In other words, by using an effective detector spacing $\delta'_{eff}$ for the actual detector spacing $\delta$, the system can be treated as a simultaneously-sampled system, even though physically, data is obtained successively.

In the ideal case of obtaining parallel-beam projections from fan-beam projections or cone-beam projections without interpolation, the detector's angular spacing $\delta$, the rotational angle sampling interval $\Delta\theta$, the rotation speed $\omega$, and the successive sampling rate $1/\tau$ satisfy the relationship:

$$\Delta\theta = q^*\delta'_{eff} = q\delta - \omega\tau, \quad (21)$$

where q is an integer and where data is sampled by the detector array in q groups with each group sampled at the time when the gantry reaches a rotation angle offset of $\delta'_{eff}$ with respect to the preceding group.

For the cone-beam scanner, the latency $\tau$ and the sampling rate $1/\tau$ refer to sampling of successive columns of the same group. The detectors at different rows of the same column can be either sampled simultaneously or sampled successively at a sub-latency per sampling substantially shorter than $\tau$.

The rotation angle interval $\Delta\theta$ is usually predetermined for a given system. If the detector's angular spacing $\delta$, the rotation speed $\omega$, and the sampling rate $1/\tau$ do not meet the ideal condition of Equation (21), certain interpolations will be required.

Suppose system conditions are not perfect, such that the value q is slightly deviated from an integer. That is:

$$q = q_o + \epsilon, \quad (22)$$

where $q_o$ is an integer and where the magnitude $\epsilon$ is much smaller than one, i.e., $|\epsilon| \ll 1$.

Interpolation of the prior art causes an undesirable filtering effect which degrades spatial resolution of the resultant image, as described above. The extent of this filtering effect depends on the magnitude of the remainder term, r, in Equation (4). From the conventional sampling sequence where all channels are sampled simultaneously:

$$-(j-j_o)/q = m + r. \quad (23)$$

Since $j - j_o$ is an integer ranging from $-N/2$ to $N/2$, r can be anywhere between 0 and 1, and the filtering effect reaches full extent.

In the sampling sequence of the present invention, the detectors are divided into $q_o$ groups, such that $$-(j'-j_o)/q_o = m, \quad (24)$$

and $$-(j'-j_o)/q = m + r. \quad (25)$$

If $1/q$ is expanded as:

$$1/q = 1/(q_o + \epsilon) \approx (1 - \epsilon/q_o)/q_o, \quad (26)$$

then Equation (25) becomes:

$$-(j'-j_o)/q \approx m + m^*\epsilon/q_o^2, \quad (27)$$

where m is an integer ranging from $-N/2q$ to $+N/2q$ and where the remainder is represented by:

$$r \approx m^*\epsilon/q_o^2. \quad (28)$$

Therefore, as long as $\epsilon \ll 1$ such that $m^*\epsilon/q_o^2$ is also much smaller than 1, r remains near zero and the filtering effect is largely reduced. The parallel-beam projection data obtained by the sampling sequence of the present invention will therefore achieve improved results over conventional sampling techniques.

In summary, the inventive data acquisition sequence described above avoids the need for interpolation during the process of reordering parallel-beam projections from fan-beam or cone-beam projections. The inventive technique is applicable when the rotation-angle sample interval $\Delta\theta$ is larger than the detector angular spacing $\delta$, and it is equally applicable to simultaneous and successive sampling. As the rotation angle interval $\Delta\theta$ increases, the merits of this inventive data acquisition sequence become more significant over the prior data acquisition sequence.

In the case of successive sampling, the rotation angle interval $\Delta\theta$ is preferably slightly deviated from the multiple integer of detector angular spacing $\delta$ to accommodate for latency $\tau$ in the sampling of successive channels. The exact amount of this deviation depends on the gantry rotation direction and speed $\omega$. Given a constant rotation-angle interval $\Delta\theta$ and rotation speed $\omega$, the effective size of detector angular spacing $\delta$ can be varied slightly by changing the sampling rate $1/\tau$ accordingly. The optimal sampling rate is selected to meet the criteria of Equation (21), in which every channel is sampled at its ideal projection angle. In this case, interpolation is avoided completely.

While this invention has been particularly shown and described with references to preferred embodiments thereof, it will be understood by those skilled in the art that various changes in form and details may be made therein without departing from the spirit and scope of the invention as defined by the appended claims.

For example, the technique of the present invention is equally applicable to helical scan systems where the object translates along the rotating axis, and non-helical scan systems where the object is stationary during a scan. Further, the principles can be applied to fourth generation CT scanners.

I claim:

1. A method of collecting data from a plurality of detector channels of a detector array during a CT scan of the type where at least a source of a diverging beam of radiation projected toward the detector array is rotatable about a rotation axis through a plurality of rotation angles ($\theta$), comprising:

collecting data from the detector channels in a predetermined sequence so that all of the data represents parallel projection data at the projection angles without the need to interpolate any of the parallel projection data;

wherein the angle ($\delta$) subtended by the part of the beam projected toward each of the detector channels is smaller than the incremental angle ($\Delta\theta$) between successive rotation angles.

2. A method according to claim 1, wherein the incremental angle $\Delta\theta = q\delta$, "q" being a whole integer greater than 1.

3. A method according to claim 2, wherein the detector channels are divided into "q" groups, the step of collecting data includes the step of collecting data from one group at each rotation angle.

4. A method according to claim 3, the step of collecting includes the step of sequentially collecting data from the groups as the source successively rotates about a rotation axis through "q" rotation angles ($\theta$).

5. A method according to claim 4, further including the step of repeating the step of sequentially collecting data substantially throughout a scan.

6. A method according to claim 3, wherein the step of collecting data includes simultaneously sampling all the detector channels within a group during each corresponding time interval.

7. A method according to claim 3, wherein the step of collecting data includes sampling all the detector channels within a group in a predetermine sequence during a corresponding time interval as the source of the diverging beam of radiation rotates about the rotation axis through each of the rotation angles.

8. A method according to claim 7, wherein the angle ($\delta$) subtended by the part of the beam projected toward each of the detector channels, the incremental angle ($\Delta\theta$) between rotation angles, rotation speed $\omega$ at which the source rotates about the rotation axis, and the sampling rate $1/\tau$ satisfy the following relationship:

$$\Delta\theta = q\delta - \omega\tau.$$

9. A method according to claim 8, wherein the step of collecting data includes the step of sampling the detector channels of each group at a rotational angle offset of $\delta'_{eff}$ following the previous group, wherein $$\delta'_{eff} = \delta - \omega\tau/q.$$

10. A method according to claim 1, wherein the source of energy defines a fan beam of radiation.

11. A method according to claim 1, wherein the detector array includes a plurality of rows of detector channels and the source of energy defines a cone beam of radiation.

12. A method according to claim 1, further including the step of reordering the data collected from the detector channels in a predetermined sequence so as to provide the parallel projection data at the projection angles.

13. The method according to claim 1, wherein the data acquired from a first group of detector channels is paired and interleaved with data acquired from a second group of detector channels when the second group of detector channels are at a sub-rotation angle interval position such that the projection angle of the first group of detector channels is substantially aligned with the projection angle of the second group of detector channels for each detector channel pair.

14. The method according to claim 13, wherein one group of detector channels includes even numbered detector channels, and the second group of detector channels includes odd numbered detector channels.

15. A CT scanning system comprising:
a detector array including at least one row of detector channels;
a source of energy defining a diverging beam of radiation directed toward the array, wherein at least the source is rotatable about a rotation axis through a plurality of rotation angles ($\theta$) and the angle ($\delta$) subtended by the part of the beam projected toward each of the detector channels is smaller than the incremental angle ($\Delta\theta$) between rotation angles; and
a subsystem for acquiring data from the detector array within a predetermined time interval as the rotation of the source passes through each of the rotation angles;
wherein data is collected from the detector channels in a predetermined sequence so that all of the data represents parallel projection data at the projection angles without the need to interpolate any of the parallel projection data.

16. A CT scanner system according to claim 15, wherein the incremental angle $\Delta\theta = q\delta$, "q" being a whole integer greater than 1.

17. A CT scanner system according to claim 16, wherein the detector channels are divided into "q" groups with data being collected by one group at each rotation angle.

18. A CT scanner system according to claim 17, wherein the sequence is such that data is sequentially collected from the groups as the source successively rotates about a rotation axis through "q" rotation angles ($\theta$).

19. A CT scanner system according to claim 18, wherein all the detector channels within a group are sampled in a predetermine Sequence during each corresponding time interval.

20. A CT scanner system according to claim 19, wherein the angle subtended by the part of the beam projected toward each of the detector channels ($\delta$), the incremental angle ($\Delta\theta$) between rotation angles, rotation speed $\omega$ at which the source rotates about the rotation axis, and the sampling rate $1/\tau$ satisfy the following relationship:

$$\Delta\theta = q\delta - \omega\tau.$$

21. A CT scanner system according to claim 20, wherein each group is sampled at a rotational angle offset of $\delta'_{eff}$ following the previous group, wherein $$\delta'_{eff} = \delta - \omega\tau/q.$$

22. A CT scanner system according to claim 18, wherein the sequence is recurring substantially throughout a scan.

23. A CT scanner system according to claim 18, wherein all the detector channels within a group are sampled simultaneously during each corresponding time interval.

24. A CT scanner system according to claim 15, further including a subsystem for reordering the data collected from the detector channels in a predetermined sequence so as to provide the parallel projection data at the projection angles.

25. A CT scanner system according to claim 15, wherein the source of energy defines a fan beam of radiation.

26. A CT scanner system according to claim 15, wherein the detector array includes a plurality of rows of detector channels and the source of energy defines a cone beam of radiation.

27. A method of acquiring projection data in a computed tomography system, the system including an energy source and a detector array rotatable about an object to be imaged for interrogating the object at rotation angle intervals $\Delta\theta$, the detector array having a plurality of channels, comprising:
at each rotation angle interval, sampling first fan-beam projection data at a first group of detector channels, each projection being oriented at a projection angle different from other projections collected in the first group; and
during transition of the detector array and source to a subsequent rotation angle interval, sampling second fan-beam projection data at a second group of detector channels paired and interleaved with the first group of detector channels, when detector channels of the second group are at an angle interval position such that the projection angle of the first group of detector channels is substantially aligned with the projection angle of the second group of detector channels for each detector channel pair;
wherein the angle ($\delta$) subtended by the part of the beam projected toward each of the detector channels is smaller than the incremental angle ($\Delta\theta$) between successive rotation angles.

28. The method of claim 27, wherein the rotation angle interval $\Delta\theta$ is substantially an integer multiple q of the detector element angular spacing $\delta$, where q is greater than 2.

29. The method of claim 27, wherein all detector channels in a group are sampled simultaneously.

30. The method of claim 27, wherein all detector channels in a group are sampled successively.

31. The method of claim 27, wherein the detector array is divided into q groups of detector elements, where q is an integer greater than 2.

32. The method of claim 27, wherein the detector array comprises a single row of detector elements for fan-beam scanning.

33. The method of claim 27, wherein the detector array comprises multiple rows of detector elements for cone-beam scanning.

34. The method of claim 27, wherein the detector angular spacing $\delta$, the sampling interval $\Delta\theta$, the system rotation speed $\omega$, and the successive sampling rate $1/\tau$ satisfy the relationship:

$$\Delta\theta = q * \delta'_{\mathit{eff}} = q\delta - \omega\tau,$$

where q is an integer and where the detector elements of the detector array are divided into q groups.

35. The method of claim 34 wherein each group is sampled at a rotational angle offset of $\delta'_{\mathit{eff}}$ following the previous group, where $$\delta'_{\mathit{eff}} = \delta - \omega\tau/q.$$

36. The method of claim 27, further comprising reordering the acquired fan-beam projection data to parallel-beam projection data having substantially the same projection angle.

37. The method of claim 27, wherein the first group of detector channels comprises odd-numbered detector channels and wherein the second group of detector channels comprises even-numbered detector channels.

38. The method of claim 27, wherein the rotation angle interval $\Delta\theta$ is substantially twice the detector element angular spacing $\delta$.

39. A system for acquiring projection data in a computed tomography system including an energy source and a detector array rotatable about an object to be imaged for interrogating the object at rotation angle intervals $\Delta\theta$, the detector array having a plurality of channels, comprising:

means for sampling, at each rotation angle interval, first fan-beam projection data at a first group of detector channels, each projection being oriented at a projection angle different from other projections collected in the first group; and means for sampling, during transition of the detector array and source to a subsequent rotation angle interval, second fan-beam projection data at a second group of detector channels paired and interleaved with the first group of detector channels, when detector channels of the second group are at a sub-rotation angle interval position such that the projection angle of the first group of detector channels is substantially aligned with the projection angle of the second group of detector channels for each detector channel pair;

wherein the angle ($\delta$) subtended by the part of the beam projected toward each of the detector channels is smaller than the incremental angle ($\Delta\theta$) between successive rotation angles.

40. The system of claim 39, wherein the rotation angle interval $\Delta\theta$ is substantially twice the detector element angular spacing $\delta$.

41. The system of claim 39, wherein the rotation angle interval $\Delta\theta$ is substantially an integer multiple q of the detector element angular spacing $\delta$, where q is greater than 2.

42. The system of claim 39, wherein all detector channels in a group are sampled simultaneously.

43. The system of claim 39, wherein all detector channels in a group are sampled successively.

44. The system of claim 39, wherein the detector array is divided into q groups of detector elements, where q is an integer greater than 2.

45. The system of claim 39, wherein the detector array comprises a single row of detector elements for fan-beam scanning.

46. The system of claim 39, wherein the detector array comprises multiple rows of detector elements for cone-beam scanning.

47. The system of claim 39, wherein the detector angular spacing $\delta$, the sampling interval $\Delta\theta$, the system rotation speed $\omega$, and the successive sampling rate $1/\tau$ satisfy the relationship:

$$\Delta\theta = q * \delta'_{\mathit{eff}} = q\delta - \omega\tau,$$

where q is an integer and where the detector elements of the detector array are divided into q groups.

48. The system of claim 47, wherein each group is sampled at a rotational angle offset of $\delta'_{\mathit{eff}}$ following the previous group, where $$\delta'_{\mathit{eff}} = \delta - \omega\tau/q.$$

49. The system of claim 39, further comprising means for reordering the acquired fan-beam projection data to parallel-beam projection data having substantially the same projection angle.

* * * * *